United States Patent [19]

Yamaguchi et al.

[11] Patent Number: 5,015,579
[45] Date of Patent: May 14, 1991

[54] PRODUCTION OF (−)TRANS-2,3-EPOXYSUCCINIC ACID BY FERMENTATION

[75] Inventors: Takamasa Yamaguchi, Suita; Ikuo Nogami, Nagaokakyo, both of Japan

[73] Assignee: Takeda Chemical Industries, Ltd., Osaka, Japan

[21] Appl. No.: 13,446

[22] Filed: Feb. 10, 1987

[30] Foreign Application Priority Data

Feb. 12, 1986 [JP] Japan ................................. 61-29644
Jan. 17, 1987 [JP] Japan ................................. 62-8611

[51] Int. Cl.$^5$ .......................... C12P 17/02; C12N 1/14
[52] U.S. Cl. ..................................... 435/123; 435/254; 435/911; 435/913; 435/916; 435/932
[58] Field of Search ............... 435/123, 911, 913, 916, 435/932, 254

[56] References Cited

U.S. PATENT DOCUMENTS 2,674,561 4/1954 Moyer ................................. 435/123

OTHER PUBLICATIONS

Miller, *The Journal of Organic Chemistry*, vol. 28, No. 4, Apr. 1963, pp. 1148–1150.
Birkinshaw et al., *Biochem J.* 39, pp. 70–72, 1945.
Martin et al., *J. of Bacteriol*, vol. 70, 1955, pp. 405–414.

*Primary Examiner*—Douglas W. Robinson
*Assistant Examiner*—Irene Marx
*Attorney, Agent, or Firm*—Wenderoth, Lind & Ponack

[57] ABSTRACT

A method for producing (−)trans-2, 3-epoxysuccinic acid, which can be used as a good starting material for the sythesis of optically active compounds such as optically specific single β-lactam antibiotics, characterized in that filamentous fungi capable of producing (−)trans-2,3-epoxysuccinic acid are cultured in liquid medium while either ammonia, sodium hydroxide or potassium hydroxide is added to maintain the culture medium in a pH range of 5.0 to 7.5 throughout the culturing period.

2 Claims, No Drawings

PRODUCTION OF (−)TRANS-2,3-EPOXYSUCCINIC ACID BY FERMENTATION

The present invention is useful in a method of producing (−)trans-2,3-epoxysuccinic acid (hereinafter also referred to as the "acid"), a substance that is well known as a raw material for the synthesis of optically active compounds, by fermentation.

(−)trans-2,3-Epoxysuccinic acid is optically active, and is easily converted to β-hydroxy-L-aspartic acid under heating in aqueous ammonia solution [Journal of Medicinal Chemistry, 6, 233 (1963)]. This amino acid not only possesses antibacterial activity, but also works well as a raw material for optically specific single β-lactam antibiotics [Japanese Published unexamined patent application No. 106444/1984; Chemical and Pharmaceutical Bulletin, 33, 3798 (1985)].

As described above (−)trans-2,3-epoxysuccinic acid can be used as a good starting material for the synthesis of optically specific single β-lactam antibiotics. At the same time, it can be a compound that works well as a "chiral synton". It is therefore significant to establish an economically advantageous production method for this compound.

It is a well-known fact that (−)trans-2,3-epoxysuccinic acid is produced and accumulated in culture broth by a wide variety of filamentous fungi cultured in liquid medium [Journal of the Agricultural Chemical Society of Japan, 13,241 (1937); 14,362 (1938); 14, 1517 (1938); 16, 1015 (1940); Biochemical Journal, 39, 70 (1945); Journal of Bacteriology, 70, 405 (1955); U.S. Pat. No. 2,674,561 (1954); Journal of Medicinal Chemistry, 6, 233 (1963); Applied and Environmental Microbiology, 35, 1213 (1978)].

In any case of the fermentation described in the above literatures, however, calcium carbonate is added as a neutralizer for this acid during the cultivation period. When calcium carbonate is used as a neutralizer, the acid precipitates in the culture broth in the form of hardly water-soluble calcium salt. In cases where filamentous fungi grow in such a culture medium containing such solid matters, the viscosity of the culture broth increases to the highest degree. Under such conditions, extremely great power input is required to feed sufficient oxygen into the culture broth for fermentation. Furthermore, it is difficult to separate this acid from fungal cells and other solid matters contained in the culture medium. The following procedures are therefore generally employed to separate this acid from fungal cells and other solid matters contained in the culture medium: mineral acid is added to convert the precipitated calcium salt of this acid into a solution of this acid in the free form, the dissolved acid is separated from fungal cells and solid matters, and then the acid is either extracted using a solvent or re-precipitated in the form of calcium salt or barium salt. However, the purification of this acid by solvent extraction is economically disadvantageous because this acid is higher in partition coefficient for water than non-water solvents (ether, ethyl acetate, etc.). The reprecipitation method is also economically disadvantageous because of its complexity.

For the production of this acid in liquid medium on industrially large scale by fermentation, it is desirable that the culturing procedure be simplified, and further, the yield be improved by facilitating the isolation of the acid from the culture broth. However, such art has not been established yet.

The present inventors made studies on the production of the acid by fermentation and found that when either ammonia, sodium hydroxide or potassium hydroxide is added so that the culture medium is maintained in a pH range of 5.0 to 7.5 throughout the cultivation period, the acid is accumulated in an amount unexpectedly greater than in the case of the addition of calcium carbonate. The present inventors also found that the accumulated acid is held in solution in the culture broth obtained after the completion of the cultivation and therefore can be separated easily from fungal cells and solid matters by filtration, etc., and that when the culture filtrate is adjusted to pH approx. 2.0~3.5, either after concentration or directly, the solubility of the acid greatly decreases to facilitate the precipitation of either monoammonium, monosodium or monopotassium salt of the acid. Based on these findings, the present inventors accomplished the present invention.

Any filamentous fungi can be used for the present invention, as long as it can produce the acid. It is recommended, however, that filamentous fungi possessing production ability of not less than 1000 µg/ml for the acid be used to make the present invention rather efficient. In the present invention, the evaluation of production ability for this acid is based on the amount of the acid obtained via shaking culture at 30° C. for 6 days in liquid media which are usually employed for the fermentative cultivation of filamentous fungi capable of producing the acid, for example, a liquid medium composed of 7.0% (hereinafter % figures represent concentration in weight/volume %) of glucose, 0.1% of $KH_2PO_4$, 0.2% of $Na_2HPO_4$, 0.1% of $NH_4Cl$, 0.012% of $MgSO_4 \cdot 7H_2O$, 0.0005% of $ZnSO_4 \cdot 7H_2O$, 0.001% of $FeSO_4 \cdot 7H_2O$, 0.5% of peptone, 0.5% of $CaCO_3$ and 2% of methanol. As examples of filamentous fungi exceeding 1000 µg/ml in production ability for the acid, mention may be made of Aspergillus awamori (IFO 4122), Aspergillus clavatus (IFO 4362), Aspergillus fumigatus (IFO 7079), Byssochlamys nivea (IFO 8815), Neosartorya fischeri (IFO 8790), Paecilomyces carneus (IFO 8292), Paecilomyces elegans (IFO 6987), Paecilomyces fumoso-roseus (IFO 7072), Paecilomyces javanicus (IFO 8297), Paecilomyces farinosus (IFO 8581), and Talaromyces wortamannii (IFO 7574). All these fungi are listed in the LIST OF CULTURES, 17th edition(1984), issued by the Institute for Fermentation, Osaka, Japan, and are currently publicly available. The present invention can be practiced by culturing filamentous fungi capable of producing (−)trans-2,3-epoxysuccinic acid as shown above in liquid medium, while adding ammonia, sodium hydroxide or potassium hydroxide so that the culture medium is maintained in a pH range of 5.0 to 7.5 throughout the cultivation period.

In the culturing method of the present invention, usually, liquid media containing carbon sources, nitrogen sources, minerals, etc., for culturing microbes can be used. Substances which can be used as carbon sources, either singly or in combination, include carbohydrates, such as starch, dextrin, maltose, sucrose, glucose and fructose. Carbon source concentration may be 3~30%, preferably 10~20%. Substances which can be used as nitrogen sources include organic or inorganic substances such as peptone, corn gluten meal, corn steep liquor, defatted soybean meal, urea, ammonium sulfate, ammonium chloride and ammonium nitrate; these substances can be used either singly or in combination, where necessary. Minerals including salts of potassium, sodium, magnesium, calcium, zinc, iron, manganese, cobalt, copper, phosphoric acid, etc. can be employed, either singly or in combination, as necessary. Nitrogen source concentration can be selected in ranges used for conventional fermentation processes (usually 0.1~3.0%, preferably 0.1~1.0%), as long as it does not interfere with the objective of the present invention. And, minerals are used in a concentration selected usually from 0.01~2.0%, preferably from 0.01~1.0%.

It is recommended that cultivation be carried out under aerobic conditions, i.e., shaking culture, aerobic submerged culture, etc. Culturing temperature is usually 10°~50° C., preferably 20°~40° C. It is necessary that the culture medium be maintained at pH 5.0~7.5, preferably maintained at pH 6.0~7.0. To obtain good result in the production of this acid, pH adjustment is achieved by adding ammonia, sodium hydroxide or potassium hydroxide which may be used preferably in the form of their aqueous solutions (5~40 w/v %, preferably 30~40 w/v %). Any method of the addition of the pH-adjusting substances can be employed, as long as it ensures the maintenance of the culture medium in the above-mentioned pH range. These pH-adjusting substances can be added either little by little without interruption, or gradually and intermittently. In general, when cultured in liquid medium under aerobic conditions, filamentous fungi grow in pelletlike or pulpy form. In some cases, however, mycelial clusters become so large that they make aeration-agitation less effective, thus exerting a negative influence on material production by the fungi themselves. In cases where the pH-adjustment of culture medium is carried out by adding either ammonia or its aqueous solution during cultivation, excessive mycelial elongation is likely to occur due to the excess of ammonium ions as the nitrogen source; it is desirable that cultivation be carried out under phosphate-limited conditions to prevent this phenomenon. When sodium hydroxide, potassium hydroxide or one of their aqueous solutions is used for the pH-adjustment of culture medium, the cultivation may be carried out under phosphate-limited conditions. To make the above phosphate-limited condition, phosphates are continuously added to the culture medium during cultivation usually at a rate of 1 to 50 $\mu$g/ml/day, preferably 2 to 20 $\mu$g/ml/day, calculated on the phosphorus basis. It is also recommended, however, that the cultivation be carried out under conditions where nitrogen sources, specifically ammonium salt, are limited to the preferable range as mentioned above in nitrogen source concentration, to obtain better results.

When cultivation is carried out under the above-mentioned conditions for 2 to 6 days, preferably 4 to 6 days, (−)trans-2,3-epoxysuccinic acid is produced and accumulated to a concentration of 60~75 mg/ml. No culture medium containing the acid at such high concentration has been obtained using calcium carbonate as the neutralizer. Known means, such as solvent extraction and precipitation using calcium hydroxide or barium hydroxide, can be used to separate and purify this acid produced and accumulated in the culture medium, but they are not economically advantageous.

To separate this acid economically and advantageously, a preliminary experiment was carried out. That is, an approx. 83% aqueous solution (pH<1) of the acid was neutralized gradually at room temperature (about 25° C.) with either ammonia, sodium hydroxide or potassium hydroxide or one of their aqueous solutions.

The solubility of the acid reached a minimum at pH near 2.0~2.5 in the case of neutralization with ammonia; at pH near 2.5~3.0 in the case of neutralization with sodium hydroxide; and at pH near 2.0~3.5 in the case of neutralization with potassium hydroxide. For each case, the crystal which formed at the pH level at which the minimum solubility appeared was separated by filtration and investigated by elemental analysis. As a result, it was found that the crystals were respectively the monoammonium salt, monosodium salt and monopotassium salt of (−)trans-2,3-epoxysuccinic acid. Applying this finding to each type of neutralized culture medium, the present inventors developed a simple separation/purification method for this acid consisting of filtration, pH adjustment (concentration, if necessary) and crystallization. For example, fungal cells and other solid matters can be removed by filtration using an ordinary method from the culture medium obtained after the completion of cultivation in the present invention. Such filtration may be carried out in accordance with routine methods, but it is preferable that filter aids such as Hyflo Super Cel (Johns-Manville Products in U.S.A.) be used for filtration. Prior to filtration, the culture medium may be adjusted to pH 4.0~5.0 using mineral acids such as sulfuric acid and hydrochloric acid to facilitate the separation of this acid from solid matters, and/or decoloration using activated charcoal may also be carried out, if necessary. The resulting culture filtrate may be concentrated, where necessary; the resulting concentrate may be filtered to remove impurities. It is possible to precipitate the desired substance, i.e. either monoammonium salt, monosodium salt or monopotassium salt of (−)trans-2,3-epoxysuccinic acid, by adjusting the culture filtrate to pH 2.0~3.5. Mineral acids such as sulfuric acid and hydrochloric acid can be used for pH adjustment; the use of sulfuric acid is preferable. It is recommended that the pH of the culture filtrate be adjusted according to the type of the neutralizer used so that the solubility of the desired substance reaches its minimum. The precipitating desired substance can be collected by known separation means such as centrifugation and filtration.

The desired products obtained using the method of the present invention were identified as (−)trans-2,3-epoxysuccinic acid by determining their physico-chemical properties including elemental composition, melting point, optical rotation and infrared spectrum. The quantitative determination of this acid in the culture medium or in the process of its isolation was achieved by high performance liquid chromatography (mobile phase: dilute aqueous solution of perchloric acid, pH 2.1; flow rate: 1.0 ml/min; detection wavelength: 214 nm) using a column packed with sulfonated polystyrene gel (Shimadzu SCR-101H column produced by Shimadzu Corporation in Japan, 7.9 mm×30 cm). Under these conditions, the retention time of this acid was about 5.6 minutes.

The detection of (−)trans-2,3-epoxysuccinic acid was achieved by thin layer chromatography using the following procedure.

Spot the sample on a cellulose plate (Merck & Co., Inc. in U.S.A.); develop the chromatograph with a mixture of diethyl ether, formic acid and water (7:2:1) at room temperature (about 25° C.) for 3 hours, and dry the plate in air; spray a 0.05% solution of bromophenol blue in ethanol on the plate: the acid is detected as a yellow spot on a blue-green ground with an Rf value of approximately 0.74.

Since it is optically active, the (—)trans-2,3-epoxysuccinic acid obtained according to the present invention can work well as raw material for the synthesis of compounds possessing optical specificity. For example, it is converted into β-hydroxy-L-aspartic acid when heated in aqueous ammonia solution, which can be converted to single β-lactam antibiotics possessing excellent antibacterial activity (Japanese Published unexamined patent application No. 106444/1984).

The present invention is hereinafter described more concretely with some examples. In the Examples which follow, % figures are shown in weight/volume %. And, symbols in the Examples have the following meanings, respectively:

| l | liter |
|---|---|
| approx. | approximately |
| min | minute |
| rpm | rotation per minute |
| Kg | Kilogram |
| cm² | square centimeter |
| G | Gravity |
| μg | microgram |
| mg | milligram |
| ml | milliliter |

EXAMPLE 1

*Aspergillus clavatus* IFO 4362 was cultured on a slant medium composed of 10% of glucose, 1.0% of peptone, 0.2% of $KNO_3$, 0.2% of $(NH_4)H_2PO_4$, 0.05% of $MgSO_4 \cdot 7H_2O$, 0.01% of $CaCl_2$ and 2.0% of agar at 28° C. for 7 days. The spores produced were suspended in sterile water to obtain a spore suspension. Separately, 100 l of a culture medium composed of 2.0% of sucrose, 1.0% of defatted soybean meal, 0.3% of $KH_2PO_4$, 0.6% of $Na_2HPO_4 \cdot 12H_2O$, 0.1% of $NH_4Cl$, 0.012% of $MgSO_4 \cdot 7H_2O$, 0.0005% of $ZnSO_4 \cdot 7H_2O$, 0.001% of $FeSO_4 \cdot 7H_2O$, 0.2% of peptone, 0.5% of $CaCO_3$ and 0.05% of Actcol (antifoaming agent, Takeda Chemical Industries in Japan) was put into a 200 l fermentor and sterilized at 120° C. for 20 minutes. The above-mentioned spore suspension was inoculated to this fermentor in an amount of approx. $10^7$ spores and cultured at 28° C., 100 l/min aeration rate, 160 rpm agitation rate and 1 Kg/cm²G pressure for 29 hours to obtain a seed culture broth.

To the fermentation medium components to make 1,000 l of a fermentation medium composed of 15.0% of glucose (sterilized previously), 0.2% of defatted soybean meal, 0.012% of $MgSO_4 \cdot 7H_2O$, 0.001% of $FeSO_4 \cdot 7H_2O$, 0.0005% of $ZnSO_4 \cdot 7H_2O$ and 0.05% of Actcol which were put into a 2,000 l fermentor, was added water so that its whole volume was 900 l, and the resulting medium was sterilized at 120° C. for 30 minutes. 100 l of the seed culture broth described above was transferred to this fermentor and cultured while adjusting the culture medium to pH approx. 6.5 using a 26% aqueous ammonia solution. Throughout the culturing period, $KH_2PO_4$ fed continuously at a rate of 10 μg/ml/day, calculated on the phosphorus basis. After culturing at 28° C., 1,000 l/min aeration rate, 200~250 rpm agitation rate and 1 Kg/cm²G pressure for 137 hours, 75.0 mg/ml (—)trans-2,3-epoxysuccinic acid was produced as a free acid, and accumulated in the fermentation broth.

EXAMPLE 2

To the fermentation medium components to make 1,000 l of a fermentation medium composed of 16.0% of glucose (sterilized previously), 0.1% of $KH_2PO_4$, 0.2% of $Na_2HPO_4 \cdot 12H_2O$, 0.3% of $NH_4Cl$, 0.2% of peptone, 0.012% of $MgSO_4 \cdot 7H_2O$, 0.001% of $FeSO_4 \cdot 7H_2O$, 0.0005% of $ZnSO_4 \cdot 7H_2O$ and 0.05% of Actcol which were put into a 2,000 l fermentor, was added water so that its whole volume was 900 l, and the resulting medium was sterilized at 120° C. for 30 minutes. 100 l of *Aspergillus clavatus* IFO 4362 seed culture broth prepared in the same manner as in Example 1 was transferred to this fermentor, after which the mixture was cultured at 28° C., 1,000 l/min aeration rate, 200~250 rpm agitation rate and 1 Kg/cm²G pressure for 137 hours while adjusting the culture medium to pH approx. 6.5 using a 40% aqueous potassium hydroxide solution: 73.7 mg/ml (—)trans-2,3-epoxysuccinic acid was produced as the free acid and accumulated in the fermentation broth.

EXAMPLE 3

*Aspergillus clavatus* IFO 4362 was cultured in the same manner as in Example 2 except that a 30% aqueous sodium hydroxide solution was used in place of a 40% aqueous potassium hydroxide solution to maintain the culture medium at pH approx. 6.5 throughout the culturing period: a fermentation broth containing 76.1 mg/ml (—)trans-2,3-epoxysuccinic acid as the free acid was obtained.

EXAMPLE 4

1,020 l (75.0 mg/ml) of the fermentation broth obtained in Example 1 was adjusted to pH 4.5 by gradually adding approx. 12 l of 10% sulfuric acid while agitating. After heat treatment at 90° C. for 15 minutes, the fermentation broth was cooled to approx. 15° C. and kept standing overnight. 10 kg activated charcoal (Shirasagi-A, Takeda Chemical Industries in Japan) was added, and the mixture was stirred gently for 2 hours. After adding 15 kg Topco Perlite 34 (Toko Perlite Industries in Japan) of a filter aid, the mixture was filtered through an Oliver filter precoated with 45 kg Hyflo Super Cel (Johns-Manville Products in U.S.A.) to obtain 1,310 l (50.8 mg/ml) primary filtrate and filter cake. Approx. 600 l water was added to the resulting filter cake to prepare a slurry, which was then filtered through the same Oliver filter as above to obtain 740 l (11.0 mg/ml) secondary filtrate. The resulting secondary filtrate was combined with the above-mentioned primary filtrate to obtain 2,050 l (36.4 mg/ml) of a mixed filtrate.

EXAMPLE 5

1,000 l of the mixed filtrate obtained in Example 4 was concentrated to an approx. 120 l volume at 50° C. using a tubular type evaporator. The resulting concentrate, after adding 0.5 kg Hyflo Super Cel of a filter aid, was filtered using a filter press precoated with 0.5 kg Hyflo Super Cel to obtain 120 l (302.6 mg/ml) of a clear filtrate. The resulting clear filtrate was adjusted to pH 2.3 by adding approx. 30 l of 30% sulfuric acid little by little, and the resulting primary crystal was separated using a basket-type centrifuge. After washing with approx. 20 l cool water, the separated crystal was dried under vacuum at 40° C. for 20 hours to obtain 19.27 kg monoammonium (—)trans-2,3-epoxysuccinate. The analytical data for the resulting crystal are as follows:

Elemental analysis (as $C_4H_7NO_5$ in %) Calculated: C, 32.22; H, 4.73; N, 9.39; Found: C., 31.98; H, 4.89; N, 9.30;

Specific optical rotation: $[\alpha]_D^{24} - 88.9°$ (C=1.0, water);

Melting point: 178°~179° C. (decomposed).

The mother liquid and the washings were then combined together and concentrated at 50° C. to a 65 l volume, after which the resulting concentrate was cooled to room temperature (about 25° C.) and the resulting secondary crystal was separated. The separated crystal was washed with approx. 10 l cool water and then dried under vacuum at 40° C. for 20 hours to obtain 14.44 kg monoammonium (−)trans-2,3-epoxysuccinate. The analytical data for the resulting crystalline substance are as follows:

Elemental analysis (as $C_4H_7NO_5$ in %); Calculated: C, 32.22; H, 4.73; N, 9.3; Found: C, 32.29; H, 4.85; N, 9.35;

Specific optical rotation: $[\alpha]_D^{24} - 90.8°$ (C=1.0, water);

Melting point: 178°~179° C. (decomposed).

Both the primary crystal and the secondary crystal were equivalent to the standard free acid sample in retention time in high performance liquid chromatography.

EXAMPLE 6

1,030 l (73.7 mg/ml) of the potassium hydroxide neutralized fermentation broth obtained in Example 2 was treated in the same manner as in Example 4 to yield 2,100 l (35.0 mg/ml) of a mixed filtrate. 1,000 l of the resulting mixed filtrate was concentrated at 50° C. to a 300 l (116.6 mg/ml) volume. The resulting concentrate, after adding 0.5 kg Hyflo Super Cel, was filtered using a filter press precoated with 0.5 kg Hyflo Super Cel to obtain approx. 300 l (115.3 mg/ml) of a clear filtrate. The resulting clear filtrate was adjusted to pH 3.0 by adding 37% hydrochloric acid little by little, after which it was further concentrated to an approx. 100 l volume under vacuum. The resulting crystal was collected using a basket-type centrifuge and washed with approx. 20 l cool water. The resulting wet crystal was dried under vacuum at 40° C. for 30 hours to obtain 34.1 kg monopotassium (−)trans-2,3-epoxysuccinate in the form of a colorless crystal. The analytical data for the resulting crystalline substance are as follows:

Elemental analysis (as $C_4H_3O_5K$ in %); Calculated: C, 28.23; H, 1.78; K, 22.98; Found: C, 28.35; H, 1.83; (K, 22);

(Figure for K alone was determined by atomic absorption spectrophotometry.)

Specific optical rotation: $[\alpha]_D^{24} - 81.3°$ (C=1.0, water);

Melting point: 209°~213° C. (decomposed).

The high performance liquid chromatography retention time and thin layer chromatography Rf value of the resulting crystal corresponded with those of the standard free acid sample.

EXAMPLE 7

1,010 l (76.1 mg/ml) of the sodium hydroxide-neutralized fermentation broth obtained in Example 3 was treated in the same manner as in Example 4 to obtain 2,020 l (36.9 mg/ml) of a mixed filtrate. 1,000 l of the resulting mixed filtrate was concentrated at 50° C. to an approx. 90 l (407.0 mg/ml) volume. The resulting concentrate, after adding 0.5 kg Hyflo Super Cel, was filtered using a filter-press precoated with 0.5 kg Hyflo Super Cel to obtain approx. 90 l of a clear filtrate. The resulting clear filtrate was adjusted to pH 2.5 by adding 37% hydrochloric acid little by little, after which it was further concentrated to an approx. 60 l volume under vacuum and kept standing at 5° C. overnight. The resulting crystal was separated using a basket-type centrifuge and washed with approx. 15 l cool water to obtain a wet crystal. The resulting wet crystal was dried under vacuum at 40° C. for 30 hours to obtain 23.6 kg monosodium (−)trans-2,3-epoxysuccinate in the form of a colorless crystal. The analytical data for the resulting crystal are as follows:

Elemental analysis (as $C_4H_3O_5Na$ in %); Calculated: C, 31.19; H, 1.96; Na, 14.92; Found: C, 31.22; H, 1.85; (Na, 14);

(Figure for Na was determined by atomic absorption spectrophotometry.)

Specific optical rotation: $[\alpha]_D^2 - 88.2°$ (C=1.0, water);

Melting point 218°~223° C. (decomposed).

The high performance liquid chromatography retention time and thin layer chromatography Rf value of this crystal corresponded with those of the standard free acid sample.

EXAMPLE 8

*Aspergillus fumigatus* (IFO 7079), *Neosartorya fischeri* (IFO 8790), *Paecilomyces elegans* (IFO 6987), *Paecilomyces farinosus* (IFO 8581) and *Talaromyces wortamannii* (IFO 7574) were each cultured on a slant medium using the same conditions as in Example 1 to produce spores and obtain spore suspensions, respectively. Each resulting suspension, in amounts of approx. 106 spores, was inoculated to a 1 l conical flask containing 150 ml of the same seed culture medium as in Example 1 and subjected to shaking culture at 30° C. for 30 hours to obtain a seed culture broth of each fungal strain. Separately, to the fermentation medium components to make 3 l of a fermentation medium composed of 15.5% of glucose (sterilized previously), 0.2% of peptone, 0.012% of $MgSO_4 \cdot 7H_2O$, 0.0005% of $ZnSO_4 \cdot 7H_2O$, 0.001% of $FeSO_4 \cdot 7H_2O$ and 0.05% of Actcol which were put into a 5 l fermentor, was added water so that its whole volume was 2.9 l, and the resulting medium was sterilized at 120° C. for 30 minutes.

100 ml of each above-mentioned seed culture broth was transferred to this fermentor and cultured while adjusting the culture medium to pH approx. 6.5 using a 26% aqueous ammonia solution. Throughout the culturing period, $KH_2PO_4$ was fed continuously at a rate of 5 μg/ml/day, calculated on the phosphorus basis. After culturing at 30° C., 3 l/min aeration rate, 800~1,000 rpm agitation rate for 140 hours, a notable amount of (−)trans-2,3-epoxysuccinic acid was produced and accumulated in the culture broth.

The results of the cultivation are summarized in Table 1.

TABLE 1

| Fungal Strain | Amount of (−)trans-2,3-Epoxysuccinic Acid Accumulated (mg/ml) |
| --- | --- |
| *Aspergillus fumigatus* (IFO 7079) | 75.2 |
| *Neosartorya fischeri* (IFO 8790) | 67.6 |
| *Paecilomyces elegans* (IFO 6987) | 72.3 |
| *Paecilomyces farinosus* | 74.8 |

TABLE 1-continued

| Fungal Strain | Amount of (−)trans-2,3-Epoxysuccinic Acid Accumulated (mg/ml) |
|---|---|
| (IFO 8581) | |
| *Talaromyces wortamannii* (IFO 7574) | 68.7 |

EXAMPLE 9

*Byssochlamys nivea* (IFO8815) was cultured on the slant medium using the same conditions as in Example 1 to produce spores and obtain spore suspension. The resulting suspension, in amount of approx. $10^6$ spores, was inoculated to a 1 l conical flask containing 150 ml of a seed culture medium composed of 2.0% of sucrose, 0.5% of yeast extract, 1.0% of defatted soybean meal, 0.3% of $KH_2PO_4$, 0.6% of $Na_2HPO_4 \cdot 12H_2O$, 0.1% of $NH_4Cl$, 0.012% of $MgSO_4 \cdot 7H_2O$, 0.0005% of $ZnSO_4 \cdot 7H_2O$, 0.001% of $FeSO_4 \cdot 7H_2O$, 0.2% of peptone, 0.5% of $CaCO_3$ and 0.05% of Actcol (antifoaming agent, Takeda Chemical Industries in Japan) and then cultured at 30° C. for 30 hours on a rotary shaker to obtain a seed culture broth. Separately, to the fermentation medium components to make 3 l of a fermentation medium composed of 15.5% of glucose (sterilized previously), 0.5% of yeast extract, 0.2% of peptone, 0.3% of $NH_4Cl$, 0.012% of $MgSO_4 \cdot 7H_2O$, 0.0005% of $ZnSO_4 \cdot 7H_2O$, 0.001% of $FeSO_4 \cdot 7H_2O$ and 0.05% of Actcol which were put into a 5 l fermentor, was added water so that its whole medium was 2.9 l, and the resulting medium was sterilized at 120° C. for 30 minutes.

100 ml of the seed culture broth mentioned above was transferred to this fermentor and cultured while adjusting the culture medium to pH approx. 6.5 using a 30% aqueous sodium hydroxide solution. After culturing at 30° C., 3 l/min aeration rate, 800~1000 rpm agitation rate for 140 hours, 65.4 mg/ml (−)trans-2,3-epoxysuccinic acid was produced and accumulated as a free acid in the culture broth.

What we claim is:

1. A method for producing (−)trans-2,3-epoxysuccinic acid which comprises
    culturing filamentous fungi capable of producing (−)-trans-2,3-epoxysuccinic acid in a liquid medium wherein one of ammonia, sodium hydroxide or potassium hydroxide is added to maintain the culture medium in a pH range of 5.0 to 7.5 throughout the culturing period,
    wherein said filamentous fungi are selected from the group consisting of *Aspergillus clavatus* (IFO 4362), *Aspergillus fumigatus* (IFO 7079), *Neosartorya fischeri* (IFO 8790), *Paecilomyces elegans* (IFO 6987), *Paecilomyces farinosus* (IFO 8581), *Talaromyces wortamannii* (IFO 7574), and *Byssochlamys nivea* (IFO 8815).

2. A method according to claim 1, wherein the culture filtrate obtained after the completion of the cultivation is adjusted to pH 2.0 to 3.5 to precipitate and collect (−)trans-2,3-epoxysuccinic acid in the form of one of a monoammonium salt, monosodium salt or monopotassium salt.

* * * * *